United States Patent [19]

Calhoun et al.

[11] Patent Number: 5,179,023

[45] Date of Patent: Jan. 12, 1993

[54] RECOMBINANT α-GALACTOSIDASE A THERAPY FOR FABRY DISEASE

[75] Inventors: David H. Calhoun, Leonia, N.J.; George Coppola, Hartsdale, N.Y.

[73] Assignee: Research Corporation Technologies, Inc., Tucson, Ariz.

[21] Appl. No.: 520,312

[22] Filed: May 7, 1990

Related U.S. Application Data

[63] Continuation-in-part of Ser. No. 328,421, Mar. 24, 1989, abandoned.

[51] Int. Cl.$^5$ .................... C12N 15/00; C12N 9/40; C12N 15/06; C12N 15/86
[52] U.S. Cl. ............................. 435/320.1; 435/208; 435/240.1; 536/23.2; 935/23; 935/32; 935/70
[58] Field of Search ................ 435/69.1, 69.2, 172.3, 435/235, 320.1, 208; 935/32, 34, 36, 48, 57; 536/27

[56] References Cited

PUBLICATIONS

Jennifer Van Brunt (1990) "The Importance of Glycoform Heterogeneity", Bio/Technology, 8, p. 995.
Davidson et al. (1990) "Oligosaccharide Processing in the Expression of Human Plasminogen cDNA by Lepidopteran Insect (Spodoptera frugiperda) Cells", Biochemistry, 29, 5584–5590.
Davidson et al. (1991) "Asparagine-Linked Oligosaccharide Processing in Lepid-opteran Insect Cells, Temporal Dependence of the Nature of the Oligosaccharides Assembled on Asparagine-289 of Recombinant Human Plasminogen Produced in Baculovirus Vector Infected Spodoptera frugipenda (IPIB-SF-21AE) Cells", Biochemistry, 30, 6167–6174.
Davidson et al. (1991) "Oligosaccharide Structures Present on Asparagine-289 of Recombinant Human Plasminogen Expressed in a Chinese Hamster Ovary Cell Line", Biochemistry, 30, 625–633.
Bishop et al. (1981) "Affinity Purification of α-Galactosidase A from Human Spleen, Placenta and Plasma with Elimination of Pyrogen Contamination", The Journal of Biological Chemistry, 256, 1307–1316.
Desnick et al. (1979) "Enzyme Therapy in Fabry Disease: Differential in vivo Plasma Clearance and Metabolic Effectiveness of Plasma and Splenic α-Galactosidase A Isozymes" Proc. Natl. Acad. Sci. USA, 76, 5326–5330.
Goochee et al. (1990) "Environmental Effects on Protein Glycosylation", Bio/Technology, 8, 421–427.
Greenfield et al. (1988) "Expression of the Human EGF Receptor with Ligand-Stimulatable Kinase Activity in Insect Cells using a Baculovirus Vector", The EMBO Journal, 7, 139–146.
Goto et al. (1988) "Production of Recombinant Human Erythropoietin in Mammalian Cells: Host-Cell Dependency of the Biological Activity of the Cloned Glycoprotein", Bio/Technology, 6, 67–71.
Miller (1988) "Vaculoviruses as Gene Expression Vectors", Ann. Rev. Microbiol., 42, 177–199.
Rademacher et al. (1988) "Glycobiology", Ann. Rev. Biochem., 57, 785–838.
Sheares et al. (1986) "Glycosylation of Ovalbumin in a Hetereologous Cell: Analysis of Oligosaccharide Chains of the Cloned Glycoprotein in Mouse L Cells", Proc. Natl. Acad. Sci. USA, 83, 1993–1997.
Wojchowski et al. (1987) "Active Human Erythropoietin Expressed in Insect Cells using a Baculovirus Vector: A Role for N-Linked Oligosaccharide", Biochimica et Biophysica Acta, 910, 224–232.
Bishop et al. (1986) Proc. Natl. Acad. Sci. USA 83: 4859–4863.
Calhoun et al. (1985) Proc. Natl. Acad. Sci. USA 82; 7364–7368.
Hantzoupoulos et al. (1987) Gene 57: 159–169.
Luckow et al. (1988) Bio/Technology 6: 47–55.
Quinn et al. (1987) Gene 58: 177–188:
Smith et al. (1983) Mol. Cell. Biol. 3: 2156–2165.
Tsuji et al. (1987) Eur. J. Biochem. 165: 275–280.

Primary Examiner—Robert A. Wax
Assistant Examiner—Dian Cook
Attorney, Agent, or Firm—Scully, Scott, Murphy & Presser

[57] ABSTRACT

Fabry disease results from an X-linked deficiency in the enzyme α-galactosidase A. The present invention is directed to recombinant human α-galactosidase A and provides baculovirus expression vectors and recombinant virus that provide stable expression of extracellular and intracellular levels of this enzyme in an insect cell culture. The recombinant-derived enzyme can be used in enzyme replacement therapy to treat Fabry patients. Composition useful in therapeutic administration of α-galactosidase A are also provided.

20 Claims, 2 Drawing Sheets

FIG. 2

SEQUENCES REMOVED:

```
         10         20         30         40         50         60
ATCATGGAGA TAATTAAAAT GATAACCATC TCGCAAATAA ATAAGTATTT TACTGTTTTC
         70         80         90        100        110        120
GTAACAGTTT TGTAATAAAA AAACCCGAGA TCCGCGGATC CCCGGGCGAG CTCGAATTCG
        130        140        150        160        170        180
GTTAATCTTA AAAGCCCAGG TTACCCGCGG AAATTTATGC TGTCCGGTCA CCGTGACAAT
        190        200        210
GCAGCTGAGG AACCCAGAAC TACATCTGGG CTG
```

SEQUENCES INSERTED:

```
         10         20         30         40         50         60
ATCATGGAGA TAATTAAAAT GATAACCATC TCGCAAATAA ATAAGTATTT TACTGTTTTC
         70         80         90        100        110        120
GTAACAGTTT TGTAATAAAA AAACCTATAA ATATGCAGCT GAGGAACCCA GAACTACATC

TGGGCTG
``` ered
RECOMBINANT α-GALACTOSIDASE A THERAPY FOR FABRY DISEASE

This application is a continuation-in-part of U.S. Ser. No. 07/328,421 filed Mar. 24, 1989, now abandoned.

FIELD OF THE INVENTION

Fabry disease results from an X-linked deficiency in the enzyme α-galactosidase A. The present invention is directed to recombinant human α-galactosidase A and provides baculovirus expression vectors and recombinant virus that provide stable expression of extracellular and intracellular levels of this enzyme in an insect cell culture. The recombinant-derived enzyme can be used in enzyme replacement therapy to treat Fabry patients. Compositions useful in therapeutic administration of α-galactosidase A are also provided.

BACKGROUND OF THE INVENTION

Fabry disease is an X-linked inborn error of metabolism resulting from a deficiency of the lysosomal enzyme, α-galactosidase A. Deficiency of α-galactosidase A results in the accumulation of its major glycosphingolipid substrate, globotriaosylceramide and related glycolipids with terminal α-galactosidic linkages. Progressive substrate deposition, especially in the plasma and vascular endothelium, leads to ischemia and infarction with early demise due to vascular disease of the heart and kidney.

Fabry diseases is one of approximately 30 lysosomal storage diseases known to affect humans. Each of these diseases result from an inherited trait which affects the levels of enzymes in the lyosome. Tay-Sach's disease and Gauucher disease are members of this group of diseases. Since specific pathways for the uptake of these other lysosomal enzymes also exist, enzyme replacement therapy is expected to be effective in Fabry disease and could logically be expected to be successful in these other diseases as well. Although these diseases are individually rare, (e.g., several thousand patients with Fabry disease are known to occur world wide, i.e., 1 to 40,000), as a group this class of diseases accounts for a significant fraction of all inherited diseases.

Several lines of evidence suggest that enzyme replacement therapy may be beneficial for patients with Fabry disease. For example, it has been demonstrated in cell cultures of fibroblasts obtained from patients with this disease that enzyme present in the culture medium is specifically transported to lysosomes. Clinical trials of enzyme replacement therapy have been reported for patients with Fabry disease using infusions of normal plasma (Mapes et al., 1970, *Science* 169: 987-989); α-galactosidase A purified from placenta (Brady et al., 1973, *New Eng. J. Med.* 279: 1163); or α-galactosidase A purified from spleen or plasma (Desnick et al., 1979, *Proc. Natl. Acad. Sci. USA* 76: 5326-5330). In one study (Desnick et al.) intravenous injection of purified enzyme resulted in a transient reduction in the plasma levels of the substrate, globtriaosylceramide. However, due to the limited availability of the human enzyme obtained from human sources, insufficient quantities were available for further study.

The α-galactosidase A enzyme is a lysosomal enzyme which hydrolyzes globotriaosylceramide and related glycolipids which have terminal α-galactosidase linkages. It is a 45 kDa N-glycosylated protein encoded on the long arm of the X chromosome. The initial glycosylated forms ($Mr=55,000$ to $58,000$) synthesized in human fibroblasts or Chang liver cells are processed to a mature glycosylated form ($Mr=50,000$). The mature active enzyme as purified from human tissues and plasma is a homodimer. (Bishop et al., 1986, *Proc. Natl. Acad. Sci. USA* 83: 4859-4863).

A human liver cDNA for α-galactosidase A was identified in a λgt11 expression library (Calhoun et al., 1985, *Proc. Natl. Acad. Sci. USA* 82: 7364-7368), and its sequence reported by Bishop et al. The original cDNA isolated by Calhoun et al. encoded the mature amino acid sequence of α-galactosidase A but did not contain the complete signal peptide sequence of the precursor form.

The partial cDNA clone was used to construct an *E. coli* expression vector by placing the α-galactosidase A coding sequence under control of the trp promoter (Hantzopoulos et al., 1987, *Gene* 57: 159-169). The level of expression of active enzyme was sufficient to support *E. coli.* growth using an α-galactoside substrate as the sole carbon source; however, increased levels of the 45 kDa protein were not detected in Coomassie blue-stained gels upon trp promoter induction nor was biological activity detected in vitro.

A genomic clone was later isolated which carried the promoter and first exon of the protein including the full signal peptide (Quinn et al., 1987, *Gene* 58: 177-188). Clones of full length cDNAs of a precursor α-galactosidase A from human fibroblasts were reported (Tsuji et al., 1987, *Eur. J. Biochem.* 165: 275-280) and used to obtain transient expression of the enzyme in monkey COS cells. The level of enzyme activity reported was only about 40% above background.

Hence one long standing need of the prior art is to provide large quantities of active human α-galactosidase A, especially for use in enzyme replacement therapy. To achieve this goal, a full length cDNA of human α-galactosidase A is needed which can be incorporated into an expression vector under control of a strong promoter. Furthermore, this vector should provide stable expression of the cDNA and use a host system in which the processing and glycosylation may occur. Finally, biologically active enzyme must be produced. One such expression vector is provided by the baculovirus expression system of the present invention.

Baculoviruses infect Lepidopterm insects and have proven useful as recombinant expression vectors (Smith et al., 1983, *Mol. Cell. Biol.* 3: 2156-2165; Luckow et al., 1988, *Bio./Technology.* 6: 47-55). The latter of these two references provides a detailed description of the available baculovirus vectors, methodology for their use and a list of proteins which have been expressed in this system. The particular advantage of baculovirus expression systems are very high levels of production (1 mg to 500 mg of protein per liter of culture have been reported), glycosylation and processing of the so-produced proteins. The early baculovirus expression vectors employ a strong promoter for a nonessential gene, the polyhedrin gene. To facilitate cloning, a DNA sequence encoding several restriction endonuclease sites had been inserted into the polyhedrin promoter (Luckow, et al., 1988, Bio/Technology 6: 47-55). Subsequently, it was discovered that this genetically engineered promoter was less effective (2-1000 fold) than the wild type polyhedrin promoter (Page, 1987, *Nuc. Acids Res.* 17 454; Ooi et al., 1989, *J. Molec. Biol.* 210 721-736). The present invention thus employs both the genetically altered polyhedrin promoter and the wild type polyhedrin promoter to generate expression systems providing large amounts of active α-galactosidase A.

SUMMARY OF THE INVENTION

The present invention is directed to replicable expression vectors that express the human α-galactosidase A enzyme. These vectors are baculovirus derivatives which have been genetically engineered to contain a full length cDNA or recombinant DNA encoding the precursor form of α-galactosidase A. The cDNA, for example, is operably linked to the baculovirus polyhedrin promoter so that the promoter directs expression of biologically active, human α-galactosidase A under the appropriate conditions. This promoter can be either a genetically engineered polyhedrin promoter with an insertion of DNA encoding several restriction endonuclease sites or wild type polyhedrin promoter. Transformant microorganisms or cell cultures carrying these vectors are also provided by the present invention.

Another aspect of the present invention provides recombinant baculoviruses having a gene sequence for the precursor form of a human α-galactosidase A enzyme and which express high levels of said enzyme.

A further aspect of this invention provides homogenous recombinant human α-galactosidase A and antibodies directed against this enzyme or directed against any active fragment or derivative of the enzyme.

A still further aspect of the present invention provides pharmaceutical compositions comprising an effective amount of recombinant human α-galactosidase A, or an active derivative thereof, and a pharmaceutically acceptable carrier. These compositions are useful in treating diseases associated with a deficiency of this enzyme, expecially Fabry disease.

BRIEF DESCRIPTION OF THE DRAWING

FIG. 2 depicts the differences in DNA sequence between transfer vectors pCC4 (top) and pCC14 (bottom). Elimination of 93 bp from the promoter sequences of pCC4 (underlined) and replacement with 7bp (underlined) in pCC14 increases α-galactosidase A protein expression at least 2-10 fold. The ATG start codon (box) is indicated in both sequences.

DETAILED DESCRIPTION OF THE INVENTION

Figure 1:
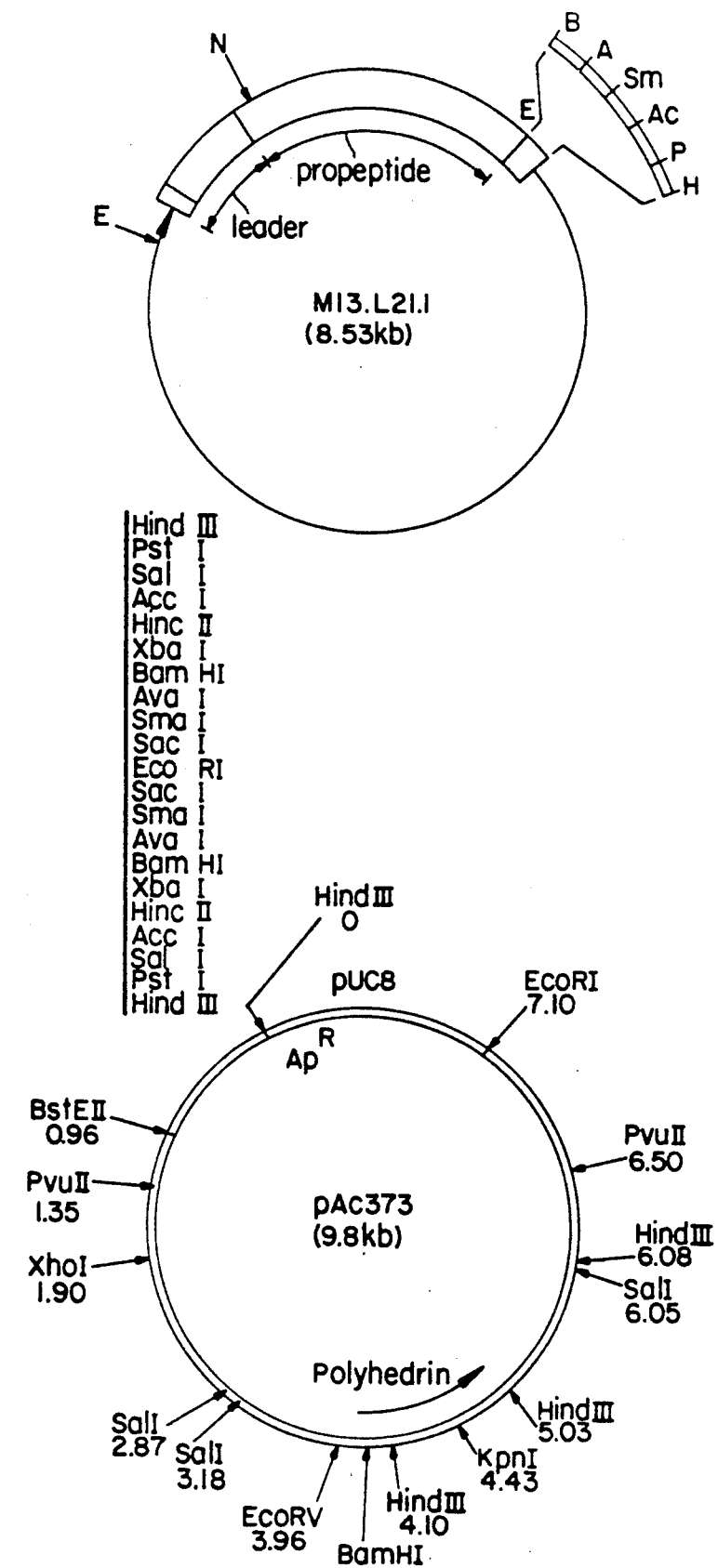
FIG. 1 depicts the human α-galactosidase cDNA features encoded on M13.L21.1 (top), the restriction enzyme recognition sites in the polylinker region of pSPR1 (middle) and a partial restriction map and some of the features of pAc373, a baculovirus transfer vector (bottom).

The present invention is directed to replicable expression vectors which are used to express human α-galactosidase A. These vectors are recombinant baculoviruses having an α-galactosidase A cDNA under control of the *Autographa californica* nuclear polyhedrosis virus (AcMNPV) polyhedrin promoter or any other strong baculovirus promoter capable of expressing foreign genes. An insect cell culture, for example *Spodoptera frugiperda* line Sf9, infected with this recombinant virus expresses α-galactosidase A both intracellularly and extracellularly at unexpected levels.

Baculovirus expression vectors and their use are reviewed in Luckow et al. The baculoviruses have double-stranded circular DNA genomes approximately 130 kb in length. These viruses have a wide host range infecting about 30 species of Lepidopterm insects. In particular, AcMNPV infection of *Spodoptera frugiperda* cell cultures produce very high levels of a protein known as polyhedrin which may account for 50% of the cellular protein. Polyhedrin is a nonessential viral gene which can be replaced by a foreign gene in order to express that gene under control of the strong polyhedrin gene promoter. The recombinant viruses are then used to infect a *S. frugiperda* cell culture to produce the desired protein. A particular advantage of this system is its similarity to higher eukaryotes with regard to protein modification, processing and transport. Thus, recombinant-derived eukaryotic proteins will be processed and glycosylated in a manner important for biological activity.

To produce a recombinant baculovirus which expresses a foreign gene, that gene is inserted into a transfer vector downstream of the polyhedrin promoter. The transfer vector is a plasmid which has been genetically engineered to contain DNA flanking the polyhedrin gene as well as convenient restriction enzyme recognition sites adjacent to the polyhedrin promoter or the polyhedrin gene initiation codon. Alternatively, the engineered polyhedrin promoter can be manipulated, e.g. its sequences changed to the original wild type or other expression-effecting sequence, to further increase expression levels. The transfer vector and viral DNA are used to co-transfect insect cell cultures. Homologous recombination will occur between the transfer vector and viral DNA during transfection and the native polyhedrin gene is replaced by the engineered polyhedrin promoter and foreign gene on the transfer vector. The viral progeny are then screened for occlusion negative (Occ⁻) virus, the phenotypic characteristic for loss of the polyhedrin gene. Occlusions are particles that appear in the cytoplasm of an infected cell and consist of virus particles embedded in a crystalline lattice of the polyhedrin protein.

The recombinant baculovirus expression vectors of the present invention are made by inserting a cDNA or a recombinant DNA for the precursor form of human α-galactosidase A downstream of the polyhedrin promoter in an baculovirus transfer vector, for example the AcMNPV transfer vector pAc373. The precursor form consists of the signal peptide and the mature α-galactosidase A. This transfer vector and many other suitable vectors are described in Luckow et al. In pAc373 there is a unique BamHI site between the polyhedrin promoter and coding region into which a DNA fragment containing the α-galactosidase A gene may be cloned.

A DNA fragment encoding the full α-galactosidase A coding sequence including the complete signal peptide is found on the EcoRI fragment from M13.L21.1. Construction of this M13 derivative is described in Hantzopoulos (1987, Ph.D. Thesis). To put BamHI ends on this EcoRI fragment, the fragment is cloned into the polylinker of pSPR1 (Krystal et al. (1986) *Proc. Natl. Acad. Sci. USA* 83: 2709-2713). Because the pSPR1 polylinker is composed of two smaller polylinkers cloned head to head at a unique EcoRI site, it provides a convenient way to introduce a variety of restriction enzyme sites on the ends of any EcoRI fragment. The BamHI fragment of the pSPR1 derivative containing the α-galactosidase A gene is then cloned into the unique BamHI site in pAc373. The resulting transfer vector, designated pCC4, contains the complete α-galactosidase A cDNA in the proper orientation relative to the polyhedrin promoter Vector pCC4 has been accorded accession number 68266 by the ATCC, 12301 Parklawn Drive, Rockville, Md. 20852.

To increase expression of α-galactosidase A the genetically engineered polyhedrin promoter in pCC4 was replaced by the wild type polyhedrin promoter (Ooi, et al., 1989, *J. Molec. Biol.* 210: 721-736). pCC4 DNA was cut with EcoRV and BssHII restriction endonucleases and the 213 bp EcoRV/BssHII fragment was discarded. This deletes 178 bp upstream and 35 bp downstream of the α-galactosidase A ATG start codon of pCC4 (See FIG. 2). To reconstruct the wild type polyhedrin promoter, and to replace the portion of the coding region lost by this deletion, 4 overlapping oligonucleotides were synthesized, annealed together and ligated into the EcoRV/BssHII cut pCC4 DNA. This new α-galactosidase A transfer vector is called pCC14. Vector pCC14 has been accorded accession number 68267 by the ATCC, 12301 Parklawn Drive, Rockville, Md. 20852. The pCC14 DNA sequences which replace the deleted DNA sequences in pCC4 are shown in FIG. 2 (differences in DNA sequence are underlined). These manipulations do not alter the ATG start codon or the coding region. The only alteration is in the length an sequence of DNA lying between the transcription start signals and the ATG start codon (7 bp in pCC14 replace 93 bp in pCC4). The DNA sequence of the pCC14 promoter was confirmed by DNA sequencing. Protein expression from pCC14 can increase up to 1000-fold for α-galactosidase A, relative to expression from pCC4.

To prepare a recombinant baculovirus derivative carrying the human α-galactosidase A gene as a cDNA, a transfer vector carrying that DNA, for example pCC4 or pCC14, and AcMNPV DNA, are used to cotransfect an insect cell culture line, preferably *S. frugiperda* cell line Sf9. The transfer vector and viral DNA undergo recombination between the homologous baculovirus sequences which flank the α-galactosidase A gene and thereby produce the desired recombinant baculovirus. To identify this recombinant baculovirus, the viral progeny from the transfection are plated on Sf9 cells and the plaques are screened to find Occ− viruses. Methods for distinguishing Occ− plaques from Occ+ plaques are described in Summers et al. (1987) *A Manual of Methods for Baculovirus Vectors and Insect Cell Culture Procedure*, Texas Agricultural Experiment Station, Bulletin No. 1555. In addition, this publication provides protocols for all of the above described manipulations and accordingly is incorporated herein by reference.

The human α-galactosidase A cDNA encoding the precursor form of this polypeptide has the following nucleotide sequence and amino acid sequence:

```
                CAGAACTACATCTGGGCTTGCGGCTTCCTGGCCCTCGTTCCTGGACATCCCTGGGCTAGAGCA          -1
                 P  E  L  H  I  L  S  C  A  L  A  L  R  F  L  A  L  V  S  W  D  I  P  S  A  R  A    -1

ATGCAGCTGAGGAACC                                                                              
 M  Q  L  R  K

CTG GAC AAT GGA TTG GCA AGG ACG CCT ACC ATG GAG CTC CAC TGG CTT GAG CTC ATG TTC AAC CTT GAC GAA GAC CCA GAT     90
Leu Asp Asn Gly Leu Ala Arg Thr Pro Thr Met Glu Leu His Trp Leu Glu Leu Met Phe Asn Leu Asp Glu Asp Pro Asp     30

TCC TGC ATC AGT GAG AAG CTC TTC ATG GTC TCA GAA GGC TGG ATG GTT CAG CGC TTC ATG AAG GAT GCA GGT GCA CTC ATT    180
Ser Cys Ile Ser Glu Lys Leu Phe Met Val Ser Glu Gly Trp Met Val Gln Arg Phe Met Lys Asp Ala Gly Ala Leu Ile     60
                      Ser                                                                               Arg

GAT GAC TGT CAC AGC GAT GCC ATG ACA CAA AGA GAT TCA GAA GGG ATT CGC TTT CCT CAG CGA TTT GAG TAT CGC CAG CTA    270
Asp Asp Cys His Ser Asp Ala Met Thr Gln Arg Asp Ser Glu Gly Ile Arg Phe Pro Gln Arg Phe Glu Tyr Arg Gln Leu     90

AAT TAT GTT CAC GAT GCT AAA AGC CAG GCC ATG CTG GAT CTG AGA CTT TAT GCA GAT CTG GGA GTT GGA CCT CAT GGC TTC    360
Asn Tyr Val His Asp Ala Lys Ser Gln Ala Met Leu Asp Leu Arg Leu Tyr Ala Asp Leu Gly Val Gly Pro His Gly Phe    120

TAC GAC ATT TAT CAC ACC CAA AGC ATT GCC CTG TTG TAC TCC CTT TTT GGA GTA ACT TAT CCA GCA GGC TTC GAT GAT GGT    450
Tyr Asp Ile Tyr His Thr Gln Ser Ile Ala Leu Leu Tyr Ser Leu Phe Gly Val Thr Tyr Pro Ala Gly Phe Asp Asp Gly    150

GAT GGT TAT AAG CAC TAT ACA GAA AAT CGA CAG TAC TGC AAT CAC GCT GAG TGG TGT GAT CCT CTT TGT AAT AGT CCC CTT    540
Asp Gly Tyr Lys His Tyr Thr Glu Asn Arg Gln Tyr Cys Asn His Ala Glu Trp Cys Asp Pro Leu Cys Asn Ser Pro Leu    180

CAA AAG CCC AAT TAT CGA CAG GAG AGA ATT GTT GAT GTT GCT GGG CCA GGG AAT GAT ATT TAT AAA TGG TTA GTG ATT GGA    630
Gln Lys Pro Asn Tyr Arg Gln Glu Arg Ile Val Asp Val Ala Gly Pro Gly Asn Asp Ile Tyr Lys Trp Leu Val Ile Gly    210
                                                                 Ala             Asp             Met

ATC TTG GAC TGG TGG ACA TCT TTT AAC CAG GAG GTA ACT CAG CAA ATG GCC ATG GCT GCC CTC TCA ATG ATA AAC GAC CTC CGA    720
Ile Leu Asp Trp Trp Thr Ser Phe Asn Gln Glu Val Thr Gln Gln Met Ala Met Ala Ala Leu Ser Met Ile Asn Asp Leu Arg    240
                                                         Glu     Ser                                 Ala

AAC TTT GGC CTC AGC TTC TGG TGG GAA CGA CTT TCC CTG GGT AAA GGA GTG GCC TGC TGT TCT AAT CCT GCT CTC TTA AAT    810
Asn Phe Gly Leu Ser Phe Trp Trp Glu Arg Leu Ser Leu Gly Lys Gly Val Ala Cys Cys Ser Asn Pro Ala Leu Leu Asn    270
                                                 Trp Gly                                                     Ala

CAC ATC AGC CCT CAA GCC TTT GAA GTG TGG TGG GAA CGG CCT CTC GGT GCC ATA ATT GCC ATC ATC AAT CAG GAC CCC ATG    900
His Ile Ser Pro Gln Ala Phe Glu Val Trp Trp Glu Arg Pro Leu Gly Ala Ile Ala Ile Ile Asn Gln Asp Pro Met    300
                                                 Lys                 Ala Ile                 Asn Glu

AGA CAG GGA GAC AAC TTT CAA GCC AAA GAC CTT CAG TGG GAG CGA CCT CTG GGT GCA GTA ATT GGC TTA GCC TGG GCA TGC    990
Arg Gln Gly Asp Asn Phe Gln Ala Lys Asp Leu Gln Trp Glu Arg Pro Leu Gly Ala Val Ile Gly Leu Ala Trp Ala Cys    330
Gln                                                     Ser
Leu                                                     Gly Lys

CCT CGC TCT TAT ACC ATC GCA GTT GCT TCC CTG GGT AAA GGA GTG GCC TGC TGT TCT AAT CCT GCT CTC TTA AAT CTT CCT GGA ATT    1080
Pro Arg Ser Tyr Thr Ile Ala Val Ala Ser Leu Gly Lys Gly Val Ala Cys Cys Ser Asn Pro Ala Leu Leu Asn Leu Pro Gly Ile    360

AGG AAG CTA TCA TAT GAA TTC TAT TCA AGA TTA AGA AGT CAC GGC ACT GTT CTT CAG CTA GAA AAT ACA GCA    1170
Arg Lys Leu Ser Tyr Glu Phe Tyr Ser Arg Leu Arg Ser His Gly Thr Val Leu Gln Leu Glu Asn Thr Ala    390

CAG ATG TCA TTA AAA GAC CTT TAAAAAAAAAAAAAAAA                                                     1209
Gln Met Ser Leu Lys Asp Leu Ter                                                                    398
```

Hence, the recombinant baculoviruses of the present invention provide high level, stable expression of biologically active human α-galactosidase A. The stable expression of high levels of biologically active human α-galactosidase A is unique to the present invention. Such expression and activity is particularly high in insect cell cultures infected with these recombinant baculoviruses in this preferred expression system, especially Sf9 cells. Recombinant α-galactosidase A activity is present in the culture medium as well as the cells, with the majority of the activity found in the culture medium. Extracellular, recombinant enzyme activity is thus achieved by the present invention. Furthermore, the expression system of the present invention provides glycosylated α-galactosidase A which is biologically active. The α-galactosidase A activity can be measured using a fluorescent substrate, 4-methylumbelliferyl-α-D-galactopyranoside, for example.

Another aspect of the present invention provides homogenous recombinant human α-galactosidase A. Homogeneous preparations are particularly useful for enzyme replacement therapy of Fabry disease and any other disease resulting from a deficiency of α-galactosidase A. Recombinant production of α-galactosidase A provides a plentiful source of active enzyme which was heretofore unavailable from natural sources or other recombinant sources. Apparently, the increased activity relative to the *E. coli* expression system already described is due to glycosylation and processing of the enzyme neither of which occurred when the α-galactosidase was expressed in *E. coli*.

Purification of recombinant α-galactosidase A from the culture medium or the intact cells, if desired, is achieved by conventional purification means such as ammonium sulfate precipitation, column chromatography and the like by following the enzymatic activity of the recombinant α-galactosidase A by the assay described herein.

One preferred scheme to purify recombinant α-galactosidase A produced by a baculovirus expression vector of the present invention involves harvesting the culture supernatent when the α-galactosidase A activity is at a peak, typically about 48 to 72 hours after viral infection of Sf9 cells. The proteins in the supernatent are precipitated by ammonium sulfate, dialyzed into an appropriate buffer and applied to a Concanavalin A-Sepharose (Pharmacia trademark) chromatography resin. The resin is eluted with 0.1M α-methylglucoside to remove contaminants and then with 1M α-methylglucoside to release the bound α-galactosidase A activity. After concentrating and dialyzing the eluate which contains the activity, it is applied to Sephadex G-200 or a DEAE-Sephadex A-50 (Pharmacia trademark) column. When applied to a DEAE column the active fractions are pooled and can be further purified on a hydroxylapatite column to an estimated 95% homogeneity.

The recombinant α-galactosidase A produced by the baculovirus expression system, e.g. in Sf9 cells, is also characterized by glycosylation. In particular, the recombinant enzyme present in culture supernatants binds to Con-A during the purification process, which indicates the presence of α-D-glucosyl or α-D-mannosyl residues on the enzyme. Moreover, treatment of a hydroxylapatite pool obtained during purification, with N-glycanase produces a marked decrease in the apparent molecular weight of the enzyme, and converts a rather diffuse band to a faster migrating and more compact band. Treatment with endoglycosidase H results in slight but reproducible changes in the migration of the enzyme in SDS gels, indicating the presence of high mannose oligosaccharide. These results are consistent with the presence of several glycoforms of the recombinant α-galactosidase A produced by insect cells, including both high mannose and complex type carbohydrate side chains.

The present invention also provides polyclonal and monoclonal antibodies to recombinant α-galactosidase A, especially from a human source. These antibodies are prepared by methods well known in the art. Extensive protocols for preparing, purifying, identifying, and use of monoclonal antibodies are found in Harlowe et al. (1988) *Antibodies: A Laboratory Manual*, Cold Spring Harbor Laboratory, Cold Spring Harbor, N.Y., 726p., which is incorporated herein by reference.

Monoclonal antibodies are conveniently prepared by immunizing mice with homogeneous or partially purified recombinant α-galactosidase A. Alternatively, fragments or active derivatives of α-galactosidase A may be used for immunization. These fragments may be made by proteolytic digestion and purified by conventional means. The enzyme derivatives may be made by chemical modification or site-directed mutagenesis of the cloned α-galactosidase A gene or cDNA. Likewise, any of these α-galactosidase A preparation are used to prepare polyclonal antibodies in rabbits or other animals such as goat, sheep, rats or the like. Methods of identifying the desired antibody include ELISA assay using any purified α-galactosidase A as the test material, Western or immunoblotting against pure or partially pure α-galactosidase A, and other methods as described in Harlowe et al. The antibodies are useful to affinity purify large quantities of α-galactosidase A, including the recombinant enzyme.

In a related embodiment, the present invention also contemplates the gene fusion of α-galactosidase A to homologous human proteins including, but not limited to, albumin, insulin and apoprotein B. Fusions may be constructed to specific fragments of these genes that stabilize the α-galactosidase A and retain specific receptors for endocytosis. This technique also contemplates the genetically altered versions of the proteins employed where, for example, it may be advantageous to eliminate the biological activity of the protein, e.g., insulin, while maintaining its intended efficacy in this context.

Another aspect of the present invention provides recombinant human α-galactosidase A as a valuable therapeutic agent for treating diseases resulting from deficiencies of this enzyme, especially Fabry disease, in a mammal by administering to said mammal an effective amount of recombinant α-galactosidase A or an active derivative or fragment thereof for a time and under conditions sufficient to treat the deficiency by increasing enzyme level.

A therapeutically effective amount of recombinant α-galactosidase A may range from about 50 to about 10,000 units enzyme activity per kg body weight per day. A unit of α-galactosidase A activity is as defined in Calhoun et al., with one unit corresponding to one nanomole of 4-methylumbelliferyl-α-D-galactopyranoside hydrolyzed per hour at 37° C.

For example, the uptake of recombinant α-galactosidase A in normal and Fabry fibroblasts can be examined to show that the recombinantly produced enzyme restores α-galactosidase A activity in cells lacking the enzyme. Restoration of function can be tested by addition of the purified enzyme to the culture medium and the results (described in detail in Example 5) indicate that recombinant α-galactosidase A is taken up in a dose dependent fashion that produces an approximately 59% increase in enzyme levels in normal fibroblasts, and a complete restoration of enzyme levels in Fabry fibroblasts. These results are quite similar to those reported for the uptake of α-galactosidase A purified from human sources (Mayes et al., 1982, *Am. J. Hum. Genet.* 34: 602–610) and indicate that the recombinant α-galactosidase A produced in this expression system is a valuable therapeutic agent for treatment of Fabry disease.

Accordingly, the subject invention contemplates treating Fabry disease or other diseases resulting from a deficiency of α-galactosidase A in mammals by administering a pharmaceutical composition containing a pharmaceutically effective amount of recombinant α-galactosidase A or an active fragment or derivative thereof. Additionally, a method for treating Fabry disease (or other diseases characterized by this enzyme deficiency) in a mammal is contemplated in which a nucleic acid molecule encoding α-galactosidase A is introduced into a cell in such a manner that said nucleic acid molecule is expressed intracellularly. By active fragments is meant any part of the enzyme which is derived from the intact whole enzyme and still retains biological activity. Likewise, derivatives of α-galactosidase mean enzymes which have been chemically modified or genetically engineered to effect minor changes, for example amino acid substitutions, which maintain biological activity. Such expression may be extrachromosomal in said cell or occur following integration into the genome of said cell. In this case where the enzyme is introduced into the cell via a nucleic acid, the nucleic acid molecule may be carried to the cell and transferred into said cell by a second nucleic acid molecule (e.g., various viruses). The first nucleic acid molecule is manipulated such that it contains the appropriate signals for expression in the target cell. That is, in accordance with the present invention, a method of treating Fabry disease in a mammal is contemplated by administering a first nucleic acid molecule encoding α-galactosidase A. This nucleic acid is contained in a pharmacologically acceptable second nucleic acid carrier such that said first nucleic acid enters a target cell and is either maintained extrachromosomally or integrated into the genome of said target. Thus, expression of the first nucleic acid produces an effective amount of human α-galactosidase A.

The active ingredients of the pharmaceutical compositions comprising recombinant α-galactosidase A are contemplated to exhibit excellent and effective therapeutic activity in replacing the enzymatic deficiency found in Fabry disease or other conditions resulting from this deficiency. Thus, the active ingredients of the therapeutic compositions including recombinant α-galactosidase A exhibit enzymatic activity when administered in therapeutic amounts from about 0.1 μg to about 2000 μg per kg of body weight per day. The dosage regimen may be adjusted to provide the optimum therapeutic response. For example, several divided doses may be administered daily or the dose may be proportionally reduced as indicated by the exigencies of the therapeutic situation. A decided practical advantage is that the active compound may be administered in a convenient manner such as by the oral, intravenous (where water soluble), intramuscular, intravenous, intranasal, intradermal, subcutaneous, or suppository routes. Depending on the route of administration, the active ingredients of recombinant α-galactosidase A-containing pharmaceutical composition may be required to be coated in a material to protect said ingredients from the action of enzymes, acids or other natural conditions.

The active compounds may also be administered parenterally or intraperitoneally. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions (where water soluble) or dispersions and sterile powders for the extemporaneous preparation of sterile injectable solutions or dispersion. In all cases the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and polyethylene glycol, and the like), suitable mixtures thereof, and vegetable oils. The proper fluidity can be maintained, for example, by the use of a coating such as lecithin, by the maintenance of the required particle size in the case of dispersion and by the use of surfactants. The preventions of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Coatings for α-galactosidase A preparations are useful to reduce degradation of the enzyme when administered as a therapeutic agent. Coatings also reduce the immunogenicity of the enzyme to help prevent undesirable side effects of administering such a therapeutic agent. A particularly useful coating to provide these characteristics is polyethylene glycol.

Sterile injectable solutions are prepared by incorporating the active compounds in the required amount in the appropriate solvent with various of the other ingredients enumerated above, as required, followed by filter sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum drying and the freeze-drying technique which yield a powder of the active ingredient plus any additional desired ingredient from previously sterile-filtered solution thereof.

When recombinant α-galactosidase A is suitably protected as described above, the active compound may be orally administered, for example, with an inert diluent or with an assimilable edible carrier, or it may be enclosed in hard or soft shell gelatin capsule, or it may be compressed into tablets, or it may be incorporated directly with the food of the diet. For oral therapeutic administration, the active compound may be incorporated with excipients and used in the form of ingestible tablets, buccal tablets, troches, capsules, elixirs, suspensions, syrups, wafers, and the like. Such compositions and preparation should contain at least 1% of active compound. The percentage of the compositions and preparations may, of course, be varied and may conveniently be between about 5 to about 80% of the weight of the unit. The amount of active compound in such therapeutically useful compositions is such that a suitable dosage is obtained. Preferred compositions or preparations according to the present invention are prepared so that an oral unit dosage form contains between about 10 ug and 1000 ug of active compound.

The tablets, troches, pills, capsules and the like may also contain the following: A binder such as gum agragacanth, acacia, corn starch or gelatin; excipients such as dicalcium phosphate; a disintegrating agent such as corn starch, potato starch, alginic acid and the like; a lubricant such as magnesium stearate; a sweetening agent such as sucrose, lactose or saccharin or a flavoring agent such as peppermint, oil of wintergreen, or cherry flavoring. When the dosage form is a capsule, it may contain, in addition to materials of the above type, a liquid carrier. Various other materials may be present as coatings or to otherwise modify the physical form of the unit dosage. For instance, tablets, pills, or capsules may be coated with shellac, sugar or both. A syrup or elixir may contain the active compound, sucrose as a sweetening agent, methyl and propylparabens as preservatives, a dye and flavoring such as cherry or orange flavor. Of course, any material used in preparing any dosage unit form should be pharmaceutically pure and substantially non-toxic in the amounts employed. In addition, the active compound may be incorporated into sustained-release preparations and formulations.

It is especially advantageous to formulate parenteral compositions in dosage unit form for ease of administration and uniformity of dosage. Unit dosage form as used herein refers to physically discrete units suited as unitary dosages for the mammalian subjects to be treated; each unit containing a predetermined quantity of active material calculated to produce the desired therapeutic effect in association with the required pharmaceutical carrier. The specification for the novel dosage unit forms of the invention are dictated by and directly dependent on (a) the unique characteristics of the active material and the particular therapeutic effect to be achieved, and (b) the limitations inherent in the art of compounding such an active material for the treatment of disease in living subjects having a diseased condition in which bodily health impaired as herein disclosed in detail.

The principal active ingredient, especially, recombinant α-galactosidase A, is compounded for convenient and effective administration in pharmaceutically effective amounts with a suitable pharmaceutically acceptable carrier in dosage unit form as hereinbefore disclosed. A unit dosage form can, for example, contain the principal active compound in amounts ranging from 10 ug to about 1000 ug. Expressed in proportions, the active compound is generally present in from about 10 ug to about 1000 ug/ml of carrier. In the case of compositions containing supplementary active ingredients, the dosages are determined by reference to the usual dose and manner of administration of the said ingredients.

As used herein, "pharmaceutically acceptable carrier" includes any and all solvents, dispersion media, coatings, antibacterial and antifungal agents, isotonic and absorption delaying agents, and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

The following examples further illustrate the invention.

EXAMPLE 1

Construction of a Baculovirus Derivative to Express Human α-Galactosidase A:

The clone that contains the complete coding region for the precursor form of human α-galactosidase A, M13..L21.1 (Hanztopoulos) was digested with EcoRI. All restriction enzyme digestions were performed according to manufacturers instructions, New England Biolabs. This EcoRI digestion was ethanol precipitated and mixed with EcoRI-digested pSPR1 in ligation buffer. After ligation with T4 DNA ligase as recommended by the manufacturer (New England Biolab), recombinants were selected for ampicillin resistance and restriction mapped to identify a pSPR1 recombinant with the EcoRI fragment having the human α-galactosidase A coding sequence. The pSPR1 derivative was then digested with BamHI and mixed with BamHI-digested pAc373, the baculovirus transfer vector which has a unique Bam HI site 8 bp upstream from the ATG codon of the polyhedrin gene coding region. After ligation, recombinants were selected for ampicillin resistance, and restriction mapped to identify two clones having the pSPR1-derived BamHI fragment inserted into the BamHI site of pAc373 in opposite orientations. These clones are the transfer vectors pCC4 which has the α-galactosidase A cDNA in the orientation properly aligned the polyhedrin promoter and pCC5 which has the cDNA in the opposite orientation. The vector pCC5 is a control plasmid.

Transfer vector pCC4 or pCC5 were co-transfected with AcMNPV DNA into S. frugiperda Sf9 cells by the methods described in Summers et al. About 3% of the plaques were Occ⁻. Several recombinant viral clones were plaque purified three times from the Occ⁻ clones. The resulting recombinant baculoviruses from transfer vector pCC4 are designated AcCC1 and AcCC2. Recombinant baculoviruses AcCC1 and AcCC2 have been accorded accession numbers VR 2268 and VR 2269, respectively, by the ATCC, 12301 Parklawn Drive, Rockville, Md. 20852. The control recombinant virus from transfer vector pCC5 is designated AcCC3.

Restriction maps of M13.L21.1 and pAc373 are shown in FIG. 1 (top and bottom). The center portion of FIG. 1 depicts the polylinker region of pSRP1.

EXAMPLE 2

Expression of Human α-Galactosidase A by Recombinant Baculovirus Vectors

To test for α-galactosidase A production, the recombinant viruses were used to infect Sf9 cells. Cells were cultured and infections carried out as described in Summers et al. Exponential phase infected cells were harvested, separated from the culture medium, and both the cells and the culture medium tested for α-galactosidase A activity. The wild type virus, AcMNPV and mock infected cells were included as controls. The activity of α-galactosidase A was measured using the fluorescent substrate, 4-methylumbelliferyl-α-D-galactopyrassoside and is expressed as units (nanomoles per hour at 37° C.) present in the cells or culture medium in a 25 cm² flask containing 5 ml of medium and approximately 3×10⁶ cells.

Table 1 indicates that recombinant viruses AcCC1 and AcCC2 express high levels of active recombinant human α-galactosidase A in the culture medium and significant levels in the cells. In contrast, the control viruses AcCC3, and AcMNPV as well as mock infections have relatively little enzyme activity. The recombinant viruses AcCC1 and AcCC2 express about 1000-fold higher levels of enzyme activity than the recombinant control virus, AcCC3.

Further, since α-galactosidase A activity is found in the culture medium, it suggests that the precursor form is properly processed to the mature form.

EXAMPLE 3

Construction and Expression of Human α-Galactosidase A in a Modified Baculovirus Vector Transfer vector pCC4, containing the human α-galactosidase A cDNA cloned in proper orientation to the modified polyhedrin promoter derived from pAc373, was digested with EcoRV and BssHII (enzymes and used as recommended by the manufacturer, New England Biolabs). The 213 bp EcoRV/BssHII fragment was discarded. To construct the wild type polyhedrin promoter, 4 overlapping oligonucleotides were synthesized, annealed together and mixed with the large fragment of EcoRV/BssHII-cut pCC4 DNA in ligation buffer. After ligation with T4 DNA ligase recombinants were transformed into *E. coli* and selected on ampicillin plates. Recombinants with the wild type polyhedrin promoter were identified by their inability to hybridize (Sambrook et al., 1989, *Molecular Cloning, a Laboratory Manual* 2 pp. 8.1-15.173) to a $^{32}P$ labeled oligonucliotide probe derived from the 93 bp region of DNA deleted from pCC4 (FIG. 2, top). To confirm that the selected clone had the proper DNA sequence of the wild type promoter, double stranded recombinant DNA was sequenced using unique oligonucliotide primers homologous to sequences lying outside the altered region. Two clones were identified with the correct sequence (FIG. 2 bottom). The modified pCC4 transfer vector was named pCC14.

After co-transfection of pCC14 and viral DNA into SF9 cells as described in Example 2, virally infected cloned cells were tested for α-galactosidase A activity. The recombinant virus which has incorporated pCC14 sequences is called AcCC4 and produce at least 2-10 fold more α-galactosidase A activity than does the pCC4 containing virus AcCC1 after on round of plaque purification. Recombinant virus AcCC4 has been accorded accession number VR 2270 by the ATCC, 12301 Parklawn Drive, Rockville, Md. 20852. After three rounds of plaque purification to yield a homogeneous preparation of AcCC4, the α-galactosidase A levels can increase up to about 1000 fold relative to AcCC1-derived enzyme levels.

EXAMPLE 4

Purification of Recombinant α-Galactosidase A and Carbohydrate Characterization

To purify the recombinant human α-galactosidase A a modification of the procedure of Calhoun, et al. (1985, Proc. Natl. Acad. Sci. USA 82, 7364-7368) was used. The culture medium from SF9 cells infected with recombinant virus was collected and the enzyme precipitated with ammonium sulfate. Precipitated crude α-galactosidase A was dialyzed and applied to a Concanavalin A-Sepharose (Pharmacia) column. The column was washed with 0.1M α-methylglucoside to remove contaminants and α-galactosidase A was eluted with 1M α-methylglucoside. After concentration using an Amicon (Danvers, Mass.) concentrator with a PM-10 membrane and dialysis, the pool of active enzyme was applied to a DEAE-Sephadex A-50 (Pharmacia) column. The column was eluted with a gradient of 10 to 200 mM NaCl and the active fractions were pooled, concentrated and dialyzed. These pooled fractions were applied to a hydroxylapatite column and α-galactosidase A was eluted with a gradient of 20 to 200 mM sodium phosphate, pH 6.5. The concentrated, dialyzed α-galactosidase A from this purification scheme was judged to be 95% homogeneous by SDS gel electrophoresis.

All of the recombinant enzyme bound to the Concanavalin A column, indicating that carbohydrate residues such as α-D-glucosyl or α-D-mannosyl were present on the enzyme. To further investigate the glycosylation of α-galactosidase A, aliquots of the purified enzyme were separately treated with two enzymes that remove selective carbohydrate moieties from the protein.

Recombinant endoglycosidase H (ICN Biomedicals, Lisle, Ill.; code number 39-131) was dissolved in 27 mM sodium phosphate buffer, pH 6.5, containing 50% glycerol at a final concentration of 1.25 units/ml. One unit of enzyme hydrolyzes one mole of $[^3H]$-dansyl-Asn(GlcNAC)$_2$ per min at 37° C. N-Glycanase (Genzyme, Boston, Mass.) was supplied as a 50% glycerol solution containing 250 units/ml. One unit of enzyme hydrolyzes one nanomole of $[^3H]$-dansyl-fetuin glycopeptide per min at 37° C. Aliquots of the enzyme obtained from the hydroxylapatite pool containing 14 μg of protein were adjusted to 0.5% NaDodSO$_4$, 0.1M β-mercaptoethanol and boiled for 2 min. The samples were then diluted to either 250 mM sodium acetate, pH 6.0 (for endoglycosidase H) or 250 mM sodium phosphate, pH 8.6 (for N-glycanase), and a final composition of 0.36% NaDodSO$_4$.2.0% NP-40, 0.07M β-mercaptoethanol. The samples were boiled again for 1 min, endoglycosidase H or N-glycanase was added to a final concentration of 0.1 unit/ml or 20 units/ml, respectively, and the samples were incubated 16 h at 37° C.

Treatment with endoglycosidase H resulted in slight but reproducible changes in the molecular weight of α-galactosidase A as judged by its migration in SDS gels, indicating the presence of mannose oligosaccharide on α-galactosidse A. Treatment of the purified enzyme with N-glycanase produced a marked decrease in the apparent molecular weight of the enzyme, and converted the rather diffuse SDS polyacrylamide band to a faster migrating and more compact band. These studies indicate α-galactosidase A is glycosylated with complex mannose containing carbohydrate moieties.

EXAMPLE 5

Uptake of Recombinant α-Galactosidase A by Normal and Fabry Fibroblasts

The uptake of the recombinant human α-galactosidase A by normal and Fabry fibroblasts in culture was determined as follows.

Fibroblasts were obtained from Fabry patients (GM2775) or normal controls (GM0500B). Monolayers were allowed to grow to 80% confluency in 25 cm² tissue culture flasks containing Delbecco's Modified Eagles (DME) Medium with 10% fetal bovine serum and antibiotics (penicillin at 100 units/ml and streptomycin at 100 ξg/ml). Before recombinant α-galactosidase addition the monolayers were rinsed three times with DME and recombinant α-galactosidase A was added to the medium. Flasks were gassed with 5% $CO_2$, sealed, and after incubation for 16 h at 27° C., the monolayers were rinsed twice with DME and trypsinized. After centrifugation the cell pellet was resuspended in 0.5 ml of buffer A containing Triton X-100 (0.1%), and the cells were disrupted by freeze-thawing three times. Protein and α-galactosidase A activity were assayed in the resultant whole cell extract.

The results shown in Table 2 indicate that the recombinant α-galactosidase A is taken up in a dose dependent fashion that results in an approximately 59% increase in enzyme levels in normal fibroblasts, and a complete restoration of enzyme levels in Fabry fibroblasts.

TABLE 1

| Virus | Transfer Vector | Enzyme Units | |
|---|---|---|---|
| | | Culture Media | Cells |
| AcCC1 | pCC4 | 2,301 | 830 |
| AcCC2 | pCC4 | 1,959 | 530 |
| AcCC3 | pCC5 | 29 | 2 |
| AcMNPV | None | 2 | 0.2 |
| Mock Infection | None | 3 | 0.4 |

TABLE 2

| Enzyme Added (units/ml) | Normal Cells (GM0500B) | Fabry Cells (GM2775) |
|---|---|---|
| None | 192 | 7 |
| 1000 | 221 | 59 |
| 2000 | 178 | 147 |
| 4000 | 306 | 270 |

What is claimed is:

1. A replicable expression vector comprising a recombinant DNA or a cDNA encoding a precursor form of biologically active alpha-galactosidase A polypeptide which is operably linked to a baculovirus nucleic acid sequence.

2. The vector of claim 1 wherein said precursor form comprises an α-galactosidase A signal peptide and the mature α-galactosidase A polypeptide.

3. The vector of claim 1 wherein the amino acid sequence of said alpha-galactosidase A comprises:

| | | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|---|
| | | | | P | E | L | H | L | S | C | A | L | A | L | R | F | L | A | L | V | S | W | D | I | P | Q | L | R | K | A |
| Leu | Asp | Asn | Gly | Leu | Ala | Arg | Thr | Pro | Thr | Met | Gly | Trp | Leu | His | Trp | Glu | Arg | Phe | Met | Cys | Asn | Leu | Asp | Cys | Met | Pro | Gln | Glu | Leu | Asp | 30 |
| Ser | Cys | Ile | Ser | Glu | Lys | Leu | Phe | Met | Glu | Met | Met | Glu | Leu | Met | Val | Ser | Glu | Gly | Trp | Lys | Asp | Ala | Gly | Tyr | Pro | Glu | Tyr | Arg | Cys | Ile | 60 |
| Asp | Asp | Tyr | Val | Met | Ala | Pro | Gln | Arg | Asp | Ser | Ala | Gly | Arg | Leu | Gln | Ala | Asp | Pro | Gln | Arg | Phe | Pro | His | Tyr | Ile | Ile | Leu | Pro | Leu | Ala | 90 |
| Asn | Tyr | Val | His | Ser | Lys | Gly | Gln | Lys | Leu | Gly | Ile | Tyr | Ala | Asp | Val | Gly | Asn | Lys | Thr | Cys | Ala | Gly | Phe | Gly | Arg | Ser | Gln | Phe | Gly | Tyr | 120 |
| Tyr | Asp | Ile | Asp | Ala | Gln | Thr | Phe | Ala | Ala | Ile | Tyr | Val | Asp | Leu | Val | Lys | Phe | Asp | Thr | Cys | Tyr | Cys | Pro | Ser | Gly | Ser | Glu | Asn | Leu | Ala | 150 |
| Asp | Gly | Tyr | Lys | His | Met | Ser | Leu | Leu | Gly | Arg | Arg | Thr | Leu | Arg | Ser | Ile | Val | Tyr | Ser | Cys | Glu | Trp | Asp | Leu | Tyr | Glu | Met | Trp | Pro | Tyr | 180 |
| Gln | Lys | Pro | Asn | Tyr | Thr | Glu | Ile | Ile | His | Asn | Trp | Arg | Phe | Ala | Pro | Ala | His | Ala | Asn | Ile | Pro | Asp | Ser | Leu | Ser | Ser | Met | Ile | Lys | Ser | 210 |
| Ile | Leu | Asp | Gln | Thr | Ser | Gln | Glu | Val | Asp | Val | Val | Ala | Ile | Pro | Gly | Asn | Gly | Ile | Ala | Trp | Asn | Asp | Pro | Trp | Met | Ser | Leu | Val | Ile | Gly | 240 |
| Asn | Phe | Gly | Ser | Ser | Trp | Glu | Gln | Met | Gln | Leu | Leu | Leu | Ala | Ile | Met | Ala | Asp | Pro | Asp | Phe | Pro | Leu | Phe | Asp | Pro | Met | Gly | Ala | Leu | Arg | 270 |
| His | Ile | Ala | Pro | Gln | Ala | Leu | Ala | Asp | Ser | Ile | Val | Ala | Ala | Val | Asn | Gly | Gln | Ala | Val | Leu | Met | Ala | Pro | Gly | Lys | Gln | Gly | Tyr | Gln | Leu | 300 |
| Arg | Gln | Asp | Tyr | Asn | Thr | Arg | Pro | Leu | Met | Lys | Leu | Lys | Val | Glu | Ala | Trp | Cys | Val | Ala | Ala | Phe | Thr | Phe | Ile | Arg | Gln | Leu | Ile | Gln | Gly | 330 |
| Pro | Arg | Tyr | Gly | Thr | Ile | Ala | Thr | Gly | Lys | Leu | Lys | Val | Gly | His | Ile | Ala | Pro | Pro | Ala | Cys | Val | Leu | Thr | Arg | Gln | Leu | Pro | Pro | Val | Lys | 360 |
| Arg | Lys | Leu | Leu | Phe | Tyr | Thr | Glu | Gln | Arg | Arg | Leu | Val | Glu | Trp | Ile | Asn | Pro | Gly | Leu | Thr | Phe | Leu | Leu | Gln | Glu | Gly | Asn | Val | Thr | Lys | 390 |
| Gln | Met | Ser | Leu | Lys | Asp | Leu | Ter | | | | | | | | | | | | | | | | | | | | | | | Met | 398 |

4. The vector of claim 1 wherein said DNA has a nucleotide sequence comprising:

```
                                                                                    ATGCAGCTGAGGAACC      -1
CAGAACTACATCTGGGCTCGCGCGCTTGCGCTTCCTGGCCCTCGTTTCCTGGGACATCCCTGGGGCTAGAGCA           90
CTG GAC AAT GGA TTG GCA AGG ACG CCT ACC ATG GGC TGG CTG CAC TGG CTT GCG CTT CCT GGC TTC ATG TGC AAC CTT GAC TGC CAG CAA CAG CCA CAT    180
TCC TGC ATC AGT GAG AAG CTC TTC ATG GAG ATG GAT TCA GAA GGC AGA GAG CTC ATG GTC TCA GAA GAC CTT GAA GGC TGG AAG GAT GCA GGT TAT GAG TAC CTC TGC ATT    270
GAT GAC TGT TGG ATG GCT CCC CAA AGA GAT CTT GAA GGC AGA GGC AGA CCT CAG GCA GAC CTT CCT CAT GGG ATT CGC GGC CTT CCT CAG CTA GCT    360
AAT TAT GTT CAC AGC AAA GGA CTG AAG CTA GGG ATT TAT GCA GAT GTT GGA AAT ACC TGC TGC TTC CCT GGC AGT TTT GAA ATT TTG GCA    450
TAC GAC ATT GAT GCC CAG ACC TTT GCT GAC TGG GGA GTA GAT CTG CTA AAA TTT GAT GGT TAC TGT GAG CCT CTT TAT ATG TGG CCC TTT    540
GAT GGT TAT AAG CAC ATG TCC TTG GCC AAT AGG ACT GGC AAT CGA CAG TAC TGC AAT ATT GTG TAC TCC TGT GAT GAT TCC TGG AAA AGT ATA AAG AGT    630
CAA AAG CCC AAT TAT ACA GAA ATC CGA CAG TAC TGC AAT CACATGG CGA AAT TTT GCT GAC ATT GAT GTT GCT GGG GGT TGG AAT GAC CCA ATC CGA GAT GGT    720
AAC TTT GGC CTC AGC TGG AAT CAG CAA GTA ACT CAG CAA GTA ATT CAG GCC ATG AGC CTC TGG CCT ATC ATG GCT GCT TTA TTC ATG TCT AAT GAC CTC CGA    810
CAC ATC AGC CCT CAA GCC AAA CCT GGC CTC AGC TGG AAT CAG CAA GCT CTC CTT CAG GAT AAG GAC GTA ATT CAG GAC GTA GCT AAT CGG CAA GGG TAC CAG CTT    900
AGA CAG GGA GAC AAC TTT GAA GTG TGG GAA CGA CCT CTC CTC ATG GCA CGG GAG ATT GGT GGA    990
CCT CGC TCT TAT GAA ATC GCA GTT GCT TCC CTG GGT AAA GGA GTG GCC TCT AAT CCT GCC TTC ATC ACA CAG ACG CTC CCT GTG AAA    1080
AGG AAG CTA GGG TTC TAT GAA GAC TTA AGA AGT CAC ATA AAT CCC ACA GGC ACT GTT TTG CTT CAG CTA GAA AAT ACA ATG    1170
CAG ATG TCA TTA AAA GAC TTA CTT TAAAAAAAAAAAAAAA    1209
```

5. The vector of claim 1 wherein said vector is a baculovirus transfer vector.

6. The vector of claim 1 wherein said vector is a recombinant baculovirus.

7. The vector of claim 6 wherein said baculovirus is *Autographa california* nuclear polyhedrosis virus.

8. The vector of claim 1 wherein said baculovirus nucleic acid sequence is the polyhedrin gene promoter.

9. The vector of claim 8 wherein the source of said promoter is the *Autographa california* nuclear polyhedrosis virus.

10. A vector of claim 1 comprising pCC4 (ATCC 68266), pCC14 (ATCC 68267), AcCC1 (ATCC VR 2268), AcCC2 (ATCC VR 2269) or AcCC4 (ATCC VR 2270).

11. The vector of any one of claims 1 to 10 wherein said α-galactosidase A is human α-galactosidase A.

12. A recombinant baculovirus comprising a nucleic acid encoding the precursor form of a biologically active α-galactosidase A.

13. A recombinant baculovirus comprising a nucleic acid encoding the mature form of a biologically active α-galactosidase A.

14. The baculovirus of claim 12 or 13 wherein the source of said α-galactosidase is a human.

15. A recombinant baculovirus comprising a nucleic acid encoding biologically active α-galactosidase A having an amino acid sequence of

| | P | E | L | H | L | S | C | A | L | A | L | R | F | L | A | L | V | S | W | D | I | P | Q | L | R | K | A | | |
|---|---|---|---|---|---|---|---|---|---|---|---|---|---|---|---|---|---|---|---|---|---|---|---|---|---|---|---|---|---|
| | | | | | | | | | | | | | | | | | | | | | | M | Q | L | R | K | A | | |
| Leu | Asp | Gly | Ala | Arg | Thr | Met | Gly | His | Leu | Arg | Glu | Phe | Arg | Leu | Trp | Leu | Asn | Cys | Met | Pro | Ser | Glu | Leu | Pro | Arg | Ala | Asp | | -1 |
| Ser | Cys | Ile | Ser | Lys | Phe | Glu | Met | Ala | Met | Val | Ser | Glu | Gly | Phe | Ala | Gly | Lys | Tyr | Leu | Glu | Pro | Cys | Ile | | | | | | 30 |
| Asp | Asp | Cys | Trp | Ala | Pro | Arg | Ser | Ala | Leu | Asp | Ala | Pro | Gly | His | Phe | Pro | Arg | Ile | Gly | Arg | Ser | Arg | Gln | Phe | Leu | Gly | Ala | | 60 |
| Asn | Tyr | Val | His | Ser | Leu | Asp | Gly | Tyr | Gly | Val | Gly | Lys | Thr | Ala | Phe | Cys | Ile | Pro | Ser | Leu | Ile | Phe | Asn | Trp | Gly | Tyr | | | 90 |
| Tyr | Asp | Ile | Asp | Lys | Ala | Asp | Leu | Val | Ile | Lys | Phe | Asp | Lys | Gly | Cys | Tyr | Asp | Pro | Leu | Tyr | Val | Glu | Ser | Met | Glu | Leu | Ala | | 120 |
| Asp | Gly | Tyr | Lys | Gln | Met | Ser | Arg | Arg | Leu | Ser | Tyr | Ala | Tyr | Glu | Cys | Glu | Ser | Leu | Tyr | Met | Lys | Ser | Met | Ser | Phe | Leu | Phe | | 150 |
| Gln | Lys | Pro | Asn | Arg | Ser | Glu | Cys | His | Trp | Arg | Asn | Phe | Tyr | Asp | Ile | Trp | Asp | Pro | Met | Ser | Leu | Met | Trp | Ile | Lys | Pro | Ser | | 180 |
| Ile | Leu | Asp | Trp | Phe | Glu | Val | Ile | Arg | Val | Ala | Pro | Gly | Ala | Trp | Asp | Ala | Asn | Ser | Leu | Ala | Asp | Val | Ile | Gly | | | | | 210 |
| Asn | Phe | Gly | Leu | Asn | Gln | Glu | Thr | Gln | Ala | Leu | Ile | Met | Gly | Ala | Pro | Leu | Phe | Met | Ser | Asn | Gly | Tyr | Asp | Leu | Gln | Arg | | | 240 |
| His | Ser | Pro | Ala | Lys | Leu | Gln | Asp | Ser | Lys | Val | Ala | Gln | Asp | Pro | Gly | Met | Lys | Arg | Asn | Ile | Thr | Ala | Ile | Met | Gln | Gly | Leu | | 270 |
| Arg | Gly | Asp | Asn | Trp | Ala | Arg | Pro | Leu | Leu | Ser | Lys | Leu | Ala | Val | Ala | Phe | Gly | Gln | Met | Gly | Leu | Ile | Gly | Leu | | | | | 300 |
| Pro | Tyr | Tyr | Phe | Ala | Ser | Arg | Gly | Lys | Lys | Gly | Ala | Met | Pro | Ala | Cys | Phe | Thr | Gln | Leu | Pro | Pro | Lys | Val | | | | | | 330 |
| Arg | Leu | Gly | Tyr | Glu | Thr | Arg | Leu | Arg | Val | Ala | Gly | Thr | Arg | Gly | Ile | Asn | Gln | Gln | Leu | Glu | Lys | Leu | Gly | Asn | Leu | Lys | Val | Thr | 360 |
| Gln | Met | Ser | Leu | Lys | Asp | Leu | Ter | | | | | | | | | | | | | | | | | | | | | | 390 |
| | | | | | | | | | | | | | | | | | | | | | | | | | | | | | 398 |

16. A recombinant baculovirus comprising a nucleic acid having a nucleotide sequence of

```
                                                                     ATGCAGCTGAGGAACC      -1
           CAGAACTACATCTGGGCTCGCGCTTCGCTTCCTGGCCCTCGTTCCTGGGACATCCCTGGGGCTAGAGCA            90
CTG GAC AAT GGA TTG GCA AGG ACG CCT ACC ATG GGC TGG CTG CAC TGG GAG CGC TTC ATG TGC AAC CTT GAC TGC CAG CAA CAG CCA CAT  180
TCC TGC ATC AGT GAG AAG CTC TTC ATG GAG ATG GCA GAG CTC TCA GAA GGC TGG AAG GAT GCA GGT TAT GAG TAC CTC TGC ATT          270
GAT GAC TGT TGG ATG GCT CCC CAA AGA GAT TCA GAA GGC AGA CTT CAG GCA GAC CCT CAG CGC TTT CCT CAT GGG CTA GCT              360
AAT TAT GTT CAC AGC AAA GGA CTG AAG CTA GGG ATT TAT GCA GAT GTT GGA AAT ACC TGC GCA GGC TTC CCT GGA AGT TTT GGA TAC      450
TAC GAC ATT GAT GCC CAG ACC TTT GCT GAC TGG GGA GTA GAT CTG CTA AAA TTT GAT GGT TAC TGT GAG TGG CCT CTT TAT ATG TGG CCC TTT 540
GAT GGT TAT AAG CAC ATG TCC TTG GCC AAT AGG ACT GGC AAT TCC TGT GAG TAC CTC CTG ATG GCT TCC TGG AAA AGT ATA AAG AGT      630
CAA AAG CCC AAT TAT ACA GAA ATC CGA CAG TAC TGC AAT CAC TGG CGA AAT TTT GCT GAC ATT GAT GAT TCC TGG AAT CAG ATC AGG AAT  720
ATC TTG GAC TGG ACA TCT TTT AAC CAG GAG AGA ATT GTT GAT GTT GCT GGG GGT TGG AAT GAC CTA TTC ATG TCT AAT GAC CTC CGA      810
AAC TTT GGC CTC AGC TGG AAT CAG CAA GTA ACT CAG ATG GCC CTC TGG GCT ATG ATG GCT GCT CCC TTA TTC ATG TCT AAT GAC CTC CGA  900
CAC ATC AGC CCT CAA GCC AAA GCT CTC CTT CAG GAT AAG GAC ATC ATC GCA ATT AAT CAG GAC GTA ATT GGC CTT ATG ATA AAC CGG CAG GAG ATT GGT GGA  990
AGA CAG GGA GAC AAC TTT GAA GTG TGG GAA CGA CCT CTC TCA GGT GGA GTT GCT TCC CTG GGT AAA GGA GTG GCC TCT AAT CCT GCC TCT GTG AAA          1080
CCT CGC TCT TAT TAC TTT GAA ATC GCA GTT TGC TCC TGC ATC ACA GAC GTT TTG CTT CAG CTA GAA AAT ACA ATG                      1170
CAG ATG TCA TTA AAA GAC TTA CTT TAAAAAAAAAAAAAAAAAA encoding a biologically active a-galactosidase A                     1209
AGG AAG CTA GGG TTC TAT GAA TGG ACT TCA AGG TTA AGA AGT CAC ATA AAT CCC ACA GGC ACT GTT TTG CTT CAG CTA GAA AAT ACA ATG
```

17. The baculovirus of any one of claims 12, 13, 15 or 16 wherein said baculovirus is AcCC1, or AcCC2 or AcCC4.

18. An insect cell or insect cell culture comprising the replicable expression vector of any one of claims 1 to 11.

19. A cultured insect cell line comprising the recombinant baculovirus of any one of claims 12, 13, 15 or 16.

20. A cultured insect cell line comprising the recombinant baculovirus of claim 17.

* * * * *

UNITED STATES PATENT AND TRADEMARK OFFICE
CERTIFICATE OF CORRECTION

PATENT NO.   : 5,179,023
DATED        : January 12, 1993
INVENTOR(S)  : David H. Calhoun, et al.

It is certified that error appears in the above-indentified patent and that said Letters Patent is hereby corrected as shown below:

```
Column 8, line 49:  under "TAA..." insert --Ter--
Column 8, line 53;  delete "Ter" and insert
--Leu--
Column 20, line 53:  after "Leu" and before "Ter"
insert --Leu--
```

Signed and Sealed this

Fourth Day of January, 1994

Attest:

BRUCE LEHMAN

*Attesting Officer*    Commissioner of Patents and Trademarks